United States Patent [19]

Brumm

[11] Patent Number: 5,543,313
[45] Date of Patent: Aug. 6, 1996

[54] PROCESS FOR THE SEPARATION AND RECOVERY OF *ASPERGILLUS NIGER* ACID PROTEASE AND GLUCOAMYLASE

[75] Inventor: Phillip J. Brumm, Rockford, Ill.

[73] Assignee: Enzyme Bio-Systems Ltd., Beloit, Wis.

[21] Appl. No.: 265,857

[22] Filed: Jun. 27, 1994

[51] Int. Cl.$^6$ ............................ C12N 9/62; C12N 9/34; C12N 1/14

[52] U.S. Cl. ................. 435/225; 435/205; 435/256.1; 435/815

[58] Field of Search .................. 435/205, 917, 435/225, 256.1, 223, 814, 815

[56] References Cited

U.S. PATENT DOCUMENTS

| | | | |
|---|---|---|---|
| 2,121,459 | 6/1938 | Waldschmidt-Leitz et al. | 435/185 |
| 3,281,331 | 10/1966 | Bergkvist | 435/225 |
| 3,335,066 | 8/1967 | Corman | 435/96 |
| 3,345,268 | 10/1967 | Corman | 435/96 |
| 3,416,997 | 12/1968 | Barton | 435/203 |
| 3,623,955 | 11/1971 | Keay | 435/222 |
| 4,100,028 | 7/1978 | Stepanov et al. | 435/222 |
| 4,347,322 | 8/1982 | Johnson et al. | 435/179 |
| 4,518,697 | 5/1985 | Bartnik et al. | 435/254.3 |
| 4,532,213 | 7/1985 | Shetty et al. | 435/225 |

OTHER PUBLICATIONS

Tomonaga et al. (1964) *J. Gen. Appl. Microbiol.*, 10(4), "Effects of Sulfur Compounds on the Protease Formation by *Aspergillus niger*", pp. 373–386.

Tomonaga (1966) *J. Gen. Appl. Microbiol.*, 12(3), "Preferential Synthesis of Extracellular Protease by *Aspergillus niger* in Sulfur Deficiency", pp. 267–276.

Pharmacia Fine Chemicals (1980) "Ion Exchange Chromatography Principles and Methods", pp. 4–38.

Ichishima et al. (1965) *Biochim. Biophys. Acta*, 99, 360–366.

Sigma Chemical Company (1992) pp. 114 and 855.

Boehringer Mannheim (1992) pp. 33–34.

*Primary Examiner*—Michael G. Wityshyn
*Assistant Examiner*—Jon P. Weber
*Attorney, Agent, or Firm*—Brooks Haidt Haffner & Delahunty

[57] ABSTRACT

*Aspergillus niger* acid protease is prepared by treating whole glucoamylase product containing a mixture of acid protease and glucoamylase with an anion exchange medium which selectively removes acid protease from the glucoamylase, producing a glucoamylase product which is protease-free. The acid protease is then recovered from the anion exchange medium by elution with high salt or low pH solution.

10 Claims, No Drawings

PROCESS FOR THE SEPARATION AND RECOVERY OF ASPERGILLUS NIGER ACID PROTEASE AND GLUCOAMYLASE

BACKGROUND OF THE INVENTION

1. Field of the Invention

This invention relates generally to a process for the separation of acid protease from whole glucoamylase product, and more specifically to separating *Aspergillus niger* acid protease from a glucoamylase product by contacting the glucoamylase/protease mixture with an anionic exchange medium.

2. Description of the Related Art

The culture broth resulting from the fermentation of certain fungi, particularly *Aspergillus niger*, contains a mixture of various enzymes having differing activities, not necessarily compatible with one another. Although the addition of *Aspergillus niger* acid protease enzymes to a steeping solution or alcohol fermentation improves bacterial growth by increasing the availability of peptides and amino acids, this growth benefit is countered by the deleterious effects acid protease has to the glucoamylase present in the culture broths. Glucoamylases that are high in acid protease can lose activity rapidly, especially when stored at elevated temperatures, greatly decreasing the storage stability of glucoamylase products.

The instability of glucoamylase appears to be the result of hydrolysis of the glucoamylase protein by acid protease. Glucoamylase instability is still present when the fermentation broth is converted to whole glucoamylase product, which despite its name is a mixture of glucoamylase and acid protease, most of the remaining enzymes having been removed.

Accordingly, it is highly desirable to separate the glucoamylase enzymes from the destabilizing acid protease enzymes present in a fungal enzyme preparation. Reduction or elimination of acid protease from whole glucoamylase product would thus result in a more stable glucoamylase product.

Various techniques are known to purify amylases having various impurities, including acid proteases. For example, U.S. Pat. No. 2,121,459 to Waldschmidt-Leitz describes a process of increasing the ratio of amylolytic to proteolytic enzymes by adsorbing the proteases on bauxite.

U.S. Pat. No. 3,416,997 to Barton describes a process of purifying fungal alpha amylase from various fermentation products of fungi, particularly *Aspergillus oryzae*, utilizing an anionic ion-exchange material. The impurities removed by the exchanger include acid protease. Similarly, U.S. Pat. Nos. 3,335,066 and 3,345,268 to Corman describe processes for purifying an amyloglucosidase-containing fungal enzyme preparation of transglucosidase using an ion exchange resin. All of these references however, fail to disclose a means for the separation and collection of protease fungal enzymes.

U.S. Pat. No. 4,532,213 to Shetty et al. describes a method for recovering acid protease from fungal mycelia. The protease is produced during fermentation by growing the fungus in an aqueous medium, producing both glucoamylase and acid fungal protease which has become associated with the fungal mycelium. After separating the protease from the fungal mycelium, the protease is recovered by treating the mycelium/protease with a solution having a pH of about 5.0 to 6.5, and the mycelium is then separated out.

The above references, although generally recognizing the desirability of separating protease from amylase, fail to provide a technique for recovering both glucoamylase and acid protease using an anion exchange medium.

It is one object of the present invention to provide a simple and effective process for separating acid protease from glucoamylase.

Another object of the present invention is to provide simple and effective processes of separating and purifying the proteolytic protease enzyme of *Aspergillus niger* from glucoamylase without any appreciable loss in substance and activity of either.

Still another object of the present invention is to provide a more stable glucoamylase product.

SUMMARY OF THE INVENTION

The present invention is a process for the separation and recovery of *Aspergillus niger* acid protease which is produced during fermentation when whole glucoamylase is prepared. A purified glucoamylase is also produced by the process of the invention. The process involves treatment of the whole glucoamylase product, containing a mixture of glucoamylase and acid protease, with an anion exchange medium which selectively removes the acid protease, leaving the whole glucoamylase product essentially protease-free. After passing the glucoamylase product through the exchange medium, the acid protease is recovered from the exchange medium by elution with a high salt or a low pH solution.

DETAILED DESCRIPTION OF THE PREFERRED EMBODIMENTS

Acid proteases formed during the fermentative preparation of whole glucoamylase are known to decrease the storage stability of the glucoamylase. *Aspergillus niger* acid protease, which is commonly formed with whole glucoamylase, can itself be a high value added product in its purified state. Consequently, a process for separating *Aspergillus niger* acid protease from the fermentation broth or from whole glucoamylase containing a mixture of *Aspergillus niger* acid protease and glucoamylase, whereby a purified glucoamylase and a purified acid protease are both produced, should be highly desirable.

Glucoamylase comprises two components which are needed for saccharification performance. One component is the enzyme glucoamylase which is present in two isozymes, known as GAI and GAII. The second component is *A. niger* acid alpha-amylase, referred to hereinafter as alpha-holoamylase.

When certain anionic ion-exchange materials are contacted with a solution containing both whole glucoamylase and acid protease, the acid protease is selectively absorbed. Where the affinity of the protease for the ion-exchanger is high enough, all or most of the protease may thereby be removed from the whole glucoamylase product, leaving the glucoamylase effectively protease-free. The exchange medium is selected so that the acid protease elutes last, after GAI, GAII and alpha-holoamylase.

The whole glucoamylase product is passed through a bed of anionic exchange material within a tank or column to insure substantially complete removal of the acid protease from the glucoamylase. The size of the bed and amount of exchange resin used will of course vary with the circumstances as will easily be determined by those skilled in the art. The anion exchange material is selected to absorb the acid protease while only absorbing minimal amounts of glucoamylase. Naturally, the exchange capacity of anion exchange resins for removing acid protease from whole glucoamylase will vary between the particular anion exchange materials. Further, it has been found that removing protease from whole glucoamylase product rather than broth results in lower exchange material usage and more rapid processing.

The process of the present invention involves the treatment of whole glucoamylase product, preferably having in excess of 200 glucoamylase units per gram, particularly 200–400 units per gram, with a sufficient amount of anion exchanger to effectively remove the acid protease. The anion exchange resin employed must have a nitrogenous functionality which is positively charged over a pH range from about 3 to 7. The mechanism for protease removal is based on the discovery that the acid protease is more acidic than any of the carbohydrases present in the glucoamylase product, and therefore binds preferentially to the exchanger in the presence of these carbohydrases.

Suitable anionic exchange resins for use in accordance with the invention include DEAE Sephadex A-50, available from Pharmacia Biotech Inc., 800 Centennial Avenue, Piscataway, N.J. 08854 U.S.A.

The purified glucoamylase product of the invention has a slightly acidic pH of about 4.0 to 6.0. A minimum pH of about 4.0 is needed to insure binding of the protease to the exchanger, typically one should use a pH at least about one pH unit higher than the isoelectric point of the protein one wishes to capture. The maximum pH of about 6.0 reflects the limits of long term glucoamylase stability in that the glucoamylase activity is lost if the pH of operation is much higher than about 6.0.

After treatment of the whole glucoamylase product within a tank or column containing exchange material, the exchanger is preferably washed with water to recover any glucoamylase remaining in the liquid within the exchanger. After removing the purified glucoamylase product solution from the exchanger, the extracted protease may be recovered from the exchanger by treating the exchanger with a concentrated salt solution, e.g., a 0.5M to 1.0M NaCl solution. Alternatively, the protease may be recovered by treating the exchanger with a low pH solution, e.g., pH less than about 3.0. The protease then can be stabilized by adding salts, carbohydrates, pH adjustment or other means.

The process of the invention can generally be carried out at ambient temperature and at temperatures from about 0° C. to about 50° C.

The following examples illustrate specific embodiments of the present invention.

EXAMPLE 1

A 10 ml sample of G-990 glucoamylase, available from Enzyme Bio-Systems, Ltd., Englewood Cliffs, N.J. 07632 U.S.A., containing a mixture of glucoamylase and acid protease was treated in a 50 milliliter beaker, equipped with a magnetic stirring bar, with 0.1 g of the anion exchanger DEAE Sephadex A-50 (0.3 milliequivalents) for a period of 10 minutes. After filtration removal of the ion exchanger, the filtrate was assayed for protease by the AZOCOLL™ protease method as follows:

Substrate Preparation

1. Weigh 20.0±0.2 mg of AZOCOLL™ (100 to 250 mesh CalBiochem Product #194931, available from CalBiochem-NovaBiochem Corporation, 10394 Pacific Center Court, San Diego, Calif. 92121 USA) into 12×100 mm disposable tubes.

2. Add 3.00 ml of Buffer Solution pH 3.00 (Fisher Product #SB97–500, available from Fischer Scientific, 711 Forbes Avenue, Pittsburgh, Pa. 15219–4785 USA) to each tube; vortex tubes to wet all substrate. Place tubes in 40° C. water bath to attemperate.

Standard Preparation

Weigh 0.500 g of Protease Type XIII Fungal (Sigma Product P2143, 0.6 protease u/mg solid) and dissolve in 8 ml of pH 3.00 buffer; dilute to 10 ml with buffer and store on ice. The standard should be prepared and used as soon as possible; the stability of the standard has not been determined.

Assay

1. At 30 second intervals, add 50 µl of sample to tubes: buffer to two blank tubes, standard to two control tubes, and undiluted glucoamylase product to two sample tubes per glucoamylase sample. Vortex samples for 10 seconds after sample addition; do not disturb tubes after returning to bath.

2. After 15 minutes, add 1.00 ml of 1 M $Na_2CO_3$ to each tube, vortex tubes for 10 seconds, and then place in ice until the entire set of assays is complete.

3. Remove precipitate by centrifugation or filtration. Measure absorbance at 520 nm.

Calculations

COLOR YIELD=(average of control samples)×(average of blanks)/Units of control added ACID PROTEASE (u/ml)=20×[(average of sample values)× (average of blanks)/COLOR YIELD]

Notes

1. CalBiochem AZOCOLL™ gives a linear curve with protease concentration. Sigma sells a product called Azocoll; this product is a fibrous material which was not readily hydrolyzed by acid protease. DO NOT USE SIGMA AZOCOLL.

2. If desired, the assay can be performed in the conical centrifuge tubes used for Phadebas assays. Smaller tubes tend to bind too much substrate to the glass for consistent results.

3. Addition of sodium carbonate has two functions. The sodium carbonate terminates the reaction by raising the pH of the reaction mixture. It also increases the COLOR YIELD since some of the hydrolysis products of the reaction are soluble at high pH but not pH 3.00.

4. Similar results were obtained for samples which were clarified by centrifugation in a microcentrifuge, filtered through glass wood, or filtered through a 0.2 micron membrane.

No protease was detected in the glucoamylase filtrate.

EXAMPLE 2

Three 10 ml samples of G-990 glucoamylase were treated with (1) (0.03 milliequivalents) 0.12 g of DE-52, an anion exchange cellulose having diethylaminoethyl tertiary amine bonded to it (DEAE), available from Whatman Bio-Systems Inc., 9 Bridewell Place, Clifton, N.J. 07014 U.S.A., (2) 0.24 g (0.06 milliequivalents) of DE-52 and (3) 0.50 g (0.13 milliequivalents) of DE-52, each for 10 minutes. Again, the ion exchanger was removed by filtration and the filtrate assayed for protease by the AZOCOLL™ protease method. The corresponding protease removals were (1) 41%, (2) 66%, and (3) 73%, respectively. The glucoamylase was removed from the settled exchanger by recovered by treatment of the exchanger with an equal volume of 20% NaCl.

Advantages of the present invention include an improved glucoamylase product having greater stability, and recovery of acid protease. Also, recovered protease can be blended back into the glucoamylase product to standardize special high-protease glucoamylase products.

Having set forth the general nature and some examples of the invention, the scope is now more particularly set forth in the appended claims.

What is claimed is:

1. A process for separating *Aspergillus niger* acid protease from an aqueous mixture of glucoamylase and acid protease and recovering purified acid protease and purified glucoamylase, consisting essentially of the sequential steps of:
   (a) contacting the aqueous mixture with an anion exchange medium wherein the medium is selected from the group consisting of an anion exchange resin and an anion exchange cellulose and has a nitrogenous functionality which is positively charged over a pH range from about 3 to 7, to absorb the acid protease while at most minimally absorbing the glucoamylase;
   (b) recovering the purified glucoamylase from the eluant from the anion exchange medium; and
   (c) treating the anion exchange medium with a salt or acid solution to desorb and recover the purified acid protease.

2. The process of claim 1 wherein the salt solution has a molarity of about 0.5 to 1.0.

3. The process of claim 2 wherein the salt is sodium chloride.

4. The process of claim 1 wherein the salt solution has a molarity over 1.0.

5. The process of claim 4 wherein the salt is sodium chloride.

6. The process of claim 1 wherein the acid solution has a pH less than about 3.0.

7. The process of claim 1 wherein the glucoamylase in the aqueous mixture contains over 200 glucoamylase units/gram.

8. The process of claim 7 wherein the glucoamylase in the aqueous mixture contains about 200–400 glucoamylase units/gram.

9. The process of claim 1 wherein before treating the anion exchange medium with the salt of step (c), the anion exchange medium is washed with water.

10. The process of claim 1 wherein the aqueous mixture comprising glucoamylase and protease of step (a) has a pH of from about 4.0 to 6.0.

* * * * *